(12) United States Patent
Azure

(10) Patent No.: US 7,979,121 B2
(45) Date of Patent: Jul. 12, 2011

(54) METHOD AND APPARATUS FOR PHYSIOLOGICAL TREATMENT WITH ELECTROMAGNETIC ENERGY

(75) Inventor: Larry Azure, La Conner, WA (US)

(73) Assignee: Lazure Scientific, Inc., Issaquah, WA (US)

( * ) Notice: Subject to any disclaimer, the term of this patent is extended or adjusted under 35 U.S.C. 154(b) by 1152 days.

(21) Appl. No.: 11/610,456

(22) Filed: Dec. 13, 2006

(65) Prior Publication Data

US 2007/0265663 A1    Nov. 15, 2007

Related U.S. Application Data

(60) Division of application No. 10/463,197, filed on Jun. 16, 2003, now abandoned, which is a continuation-in-part of application No. 10/171,821, filed on Jun. 14, 2002, now abandoned.

(51) Int. Cl.
*A61N 1/18* (2006.01)
*A61N 1/40* (2006.01)

(52) U.S. Cl. .................. 607/3; 607/50; 607/88; 607/89

(58) Field of Classification Search ........................ None
See application file for complete search history.

(56) References Cited

U.S. PATENT DOCUMENTS

| | | |
|---|---|---|
| 3,615,454 A | 10/1971 | Cescon et al. |
| 3,680,959 A | 8/1972 | Schuch et al. |
| 3,773,049 A | 11/1973 | Rabichev et al. |
| 3,785,383 A | 1/1974 | Dotto |
| 3,867,569 A | 2/1975 | Watson |
| 3,922,061 A | 11/1975 | Glass et al. |
| 4,233,965 A | 11/1980 | Fairbanks |
| 4,505,545 A | 3/1985 | Salia-Munoz |
| 4,553,546 A | 11/1985 | Javelle |
| 4,573,465 A | 3/1986 | Sugiyama et al. |
| 4,707,698 A | 11/1987 | Constant |
| 4,741,347 A | 5/1988 | Robert et al. |
| 4,793,325 A | 12/1988 | Cadossi et al. |
| 4,901,724 A | 2/1990 | Mori |
| 4,909,255 A | 3/1990 | Farin |
| 4,911,686 A | 3/1990 | Thaler |
| 4,930,504 A | 6/1990 | Diamantopoulos et al. |
| 4,989,605 A | 2/1991 | Rossen |
| 5,024,236 A | 6/1991 | Shapiro |
| 5,074,305 A | 12/1991 | Guderian |
| 5,197,940 A | 3/1993 | Sievert et al. |
| 5,304,207 A | 4/1994 | Stromer |
| 5,307,253 A | 4/1994 | Jehn |

(Continued)

FOREIGN PATENT DOCUMENTS

DE    9209379.5    11/1992

(Continued)

*Primary Examiner* — Kennedy J Schaetzle
(74) *Attorney, Agent, or Firm* — Kilpatrick Townsend & Stockton LLP

(57) ABSTRACT

An electromagnetic device and method of operation thereof are disclosed. The electromagnetic device contains an electromagnetic field generator, a microcurrent generator and a photonic accumulator. The electromagnetic field generator generates broadband electromagnetic fields to substantially envelope a subject placed in proximity thereto. The subject is placed in contact with microcurrent electrodes so as to permit a broadband microcurrent to flow through the subject or along the surface of the subject. A photonic accumulator is positioned proximate the subject to receive biophotons emitted therefrom and to activate the biophotons with a light source.

14 Claims, 10 Drawing Sheets

U.S. PATENT DOCUMENTS

| | | | |
|---|---|---|---|
| 5,366,435 A | 11/1994 | Jacobson | |
| 5,449,376 A * | 9/1995 | Callahan | 607/2 |
| 5,453,072 A | 9/1995 | Anninos et al. | |
| 5,464,436 A * | 11/1995 | Smith | 607/89 |
| 5,519,534 A | 5/1996 | Smith et al. | |
| 5,556,418 A | 9/1996 | Pappas | |
| 5,643,333 A | 7/1997 | Yun | |
| 5,743,844 A | 4/1998 | Tepper et al. | |
| 5,800,479 A | 9/1998 | Thiberg | |
| 5,807,232 A | 9/1998 | Espinoza et al. | |
| 5,812,581 A | 9/1998 | Cox | |
| 5,824,023 A | 10/1998 | Anderson | |
| 5,843,143 A | 12/1998 | Whitehurst | |
| 6,035,141 A | 3/2000 | Constable | |
| 6,261,310 B1 | 7/2001 | Neuberger et al. | |
| 6,402,681 B1 | 6/2002 | McDonough et al. | |
| 6,443,978 B1 | 9/2002 | Zharov | |
| 6,641,578 B2 | 11/2003 | Mukai | |
| 6,706,035 B2 | 3/2004 | Cense et al. | |
| 6,796,994 B2 | 9/2004 | Ignatius et al. | |
| 2002/0120312 A1 | 8/2002 | Ignatius et al. | |
| 2002/0173780 A1 | 11/2002 | Altshuler et al. | |

FOREIGN PATENT DOCUMENTS

| | | |
|---|---|---|
| EP | 0416150 A1 | 3/1991 |
| EP | 1118311 A2 | 7/2001 |
| EP | 1147786 A2 | 10/2001 |
| GB | 2262043 | 6/1993 |
| GB | 2272278 A | 5/1994 |
| WO | WO 90/00420 | 1/1990 |
| WO | WO 98/25667 | 6/1998 |

\* cited by examiner

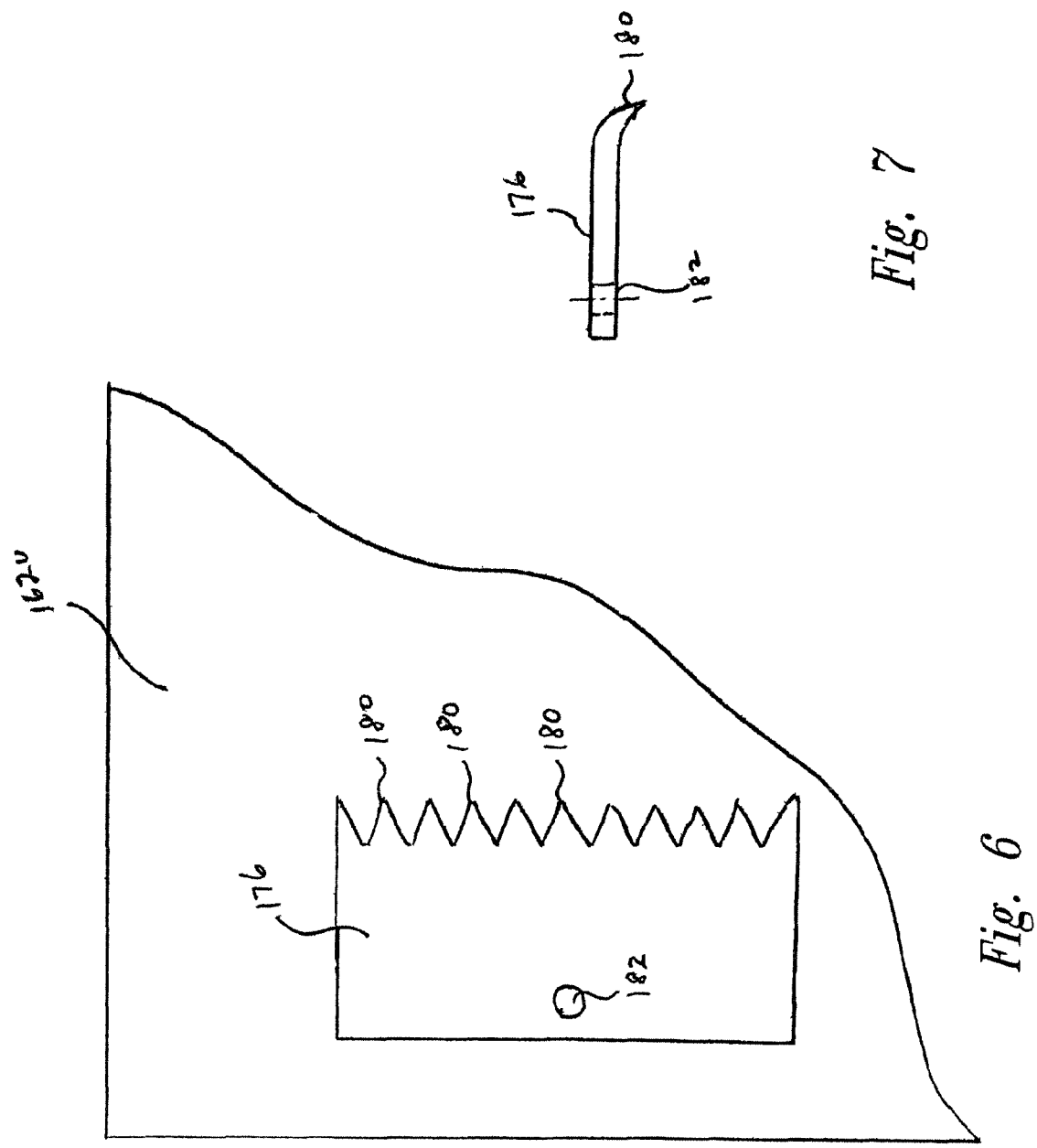

METHOD AND APPARATUS FOR PHYSIOLOGICAL TREATMENT WITH ELECTROMAGNETIC ENERGY

RELATED APPLICATIONS

This application is a divisional application of, and claims priority to, U.S. patent application Ser. No. 10/463,197 filed Jun. 16, 2003, now abandoned, which is a continuation-in-part of U.S. patent application Ser. No. 10/171,821 filed Jun. 14, 2002, now abandoned.

TECHNICAL FIELD

The present description is related generally to techniques to assist the body in self-healing and, more particularly, to a method and system for activation of healing mechanisms using electromagnetic energy.

BACKGROUND

Individual cells in a subject are electro-chemical units having a metabolic chemistry with both electrical and chemical properties. Each cell is surrounded by a membrane which acts a "battery" that is continually recharged by the metabolic chemistry of the cell. The cell supports an electrical potential across the membrane, called a transmembrane potential (TMP), which varies in a healthy cell from about 70 to 100 millivolts.

When the energy level (bioenergy) of a "sick" cell is reduced by trauma, disease, parasitic infection such as HIV or malnutrition, the TMP falls along with the biochemical metabolism, especially production of adenosine triphosphate (ATP), until the cell either recovers, undergoes mitosis or dies. Harmless irradiation of the body by exogenic, non-ionizing pulsed electromagnetic fields (PEMFs) for short periods (i.e., minutes) at long intervals (i.e., days or weeks) has been shown to be highly effective in relieving pain, healing trauma and clearing or controlling infections.

The healing of diseased or damaged cells is enhanced by the application of electrical current directly to an area of the body, or by exposing an area of the body to an electromagnetic field to induce an electrical current in the diseased or damaged cells. The added current aids healing by raising the TMP and restoring energy to the cells. The electrical current supports the exchange of potassium and sodium ions, and facilitates the production of adenosine triphosphate (ATP). Normal healthy cells are not adversely affected by the added current because a membrane with a normal TMP will not accept additional charge.

Electromagnetic fields have been applied to treat a number of diseases. For example, cancer cells have been exposed to electromagnetic fields. It is believed that, as a typical cancer cell grows, its TMP falls. The growing cancer cell will undergo mitosis when its TMP falls below a threshold. The application of an electromagnetic field can maintain the TMP of a cancer cell above the threshold to prevent the mitosis from occurring. As a result, the cancer cell grows too large for its membrane and cannot absorb sufficient nutrients to survive. Eventually, the cancer cell dies. Electromagnetic (EM) fields have also been applied to treat bacterial infections, relieve pain, and to eliminate tapeworm and hookworm infestations.

The reaction of various species of sick cells is frequency dependent. However, the frequencies required by specific cells is not readily determined. Accordingly, there is a need in the art for a system and method for treating individuals with complex frequency EM fields. The present invention provides this, and other advantages as will be apparent from the following figures and accompanying detailed description.

SUMMARY

Disclosed is an apparatus and method for physiological treatment. In an exemplary embodiment, the apparatus comprises an electromagnetic field generator and a microcurrent generator. In one embodiment the microcurrent generator is synchronized for operation with the electromagnetic field generator. In addition, a photonic accumulator may be used in conjunction with the electromagnetic field generator and the microcurrent generator or used independently of the electromagnetic field generator and the microcurrent generator.

In one embodiment, the electromagnetic field generator comprises a spark gap generator with first and second spaced apart electrodes. The spark gap generator may be coupled to a step-up transformer, such as a Tesla coil, to generate a high voltage electromagnetic field having power density across a broad portion of the spectrum.

The microcurrent generator may also comprise a spark gap device to generate broad spectrum microcurrents. The microcurrent generator may comprise a handheld electrode and a plate electrode placed in contact with the subject for a therapeutic period of time such that at least a portion of the generated microcurrent flows from the handheld electrode to the plate electrode via the subject.

The electromagnetic field generator and the microcurrent generator may be configured for in-phase operation. In a typical implementation, the electromagnetic field generator has power density ranging from less than 100 hertz to more than a gigahertz.

The photonic accumulator may comprise a housing having first aperture to permit the entry of photons emitted from the subject and a first light source. A second aperture in the housing permits entry of the light generated by the first light source. In an exemplary embodiment, the first light source is a coherent light source. The photonic accumulator may further comprise a second light source to generate light that is introduced into the housing via a third aperture. The second light source may also generate coherent light in an exemplary embodiment.

BRIEF DESCRIPTION OF THE DRAWINGS

FIG. 6 is a top plan view of a fragmentary portion of one electrode and a spark gap coupled thereto.

FIG. 7 is a side view of the spark gap of FIG. 6.

DETAILED DESCRIPTION

Figure 1:
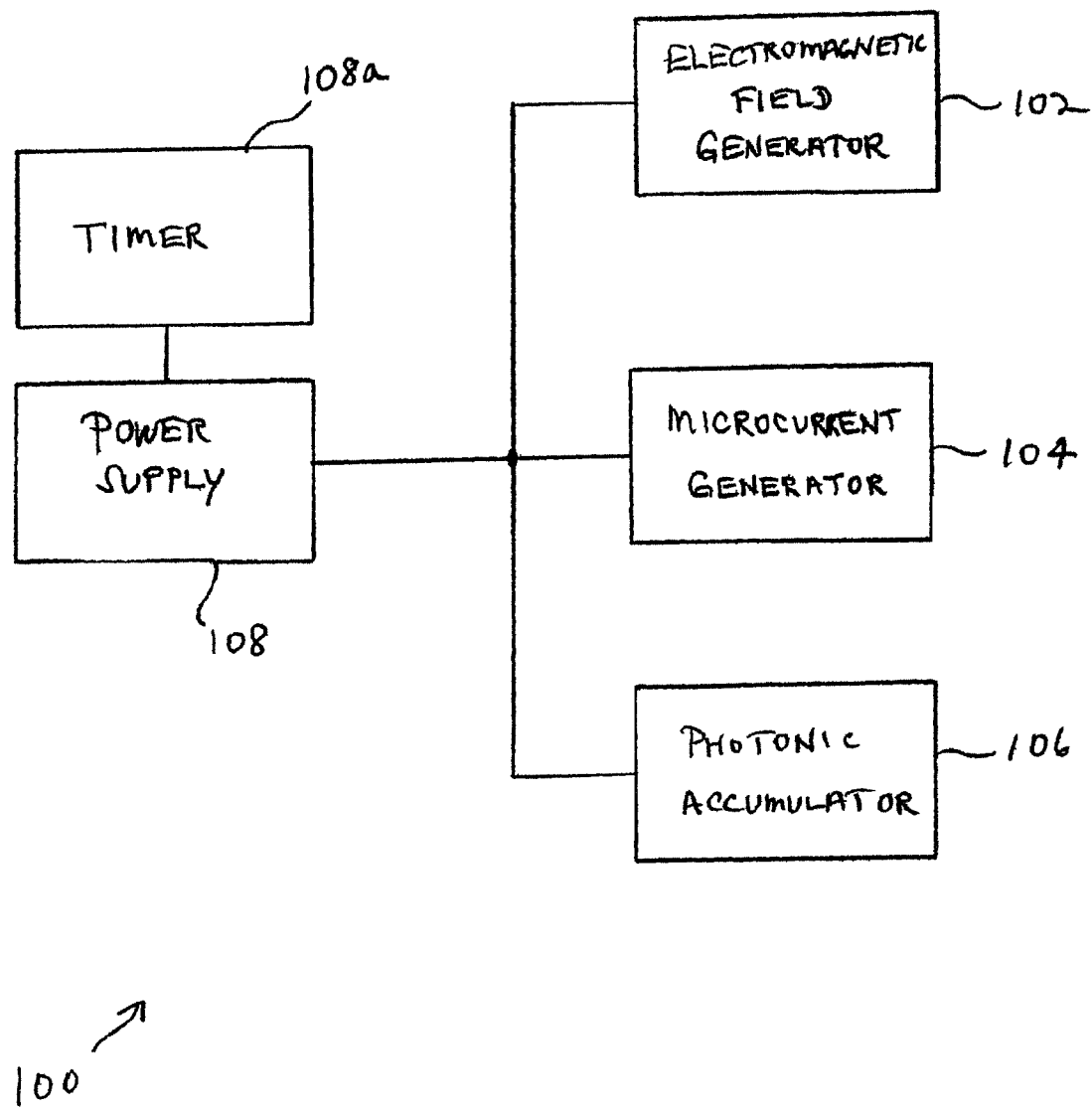
FIG. 1 is a functional bock diagram of a system constructed in accordance with the present description.

FIG. 1 is functional block diagram of a device constructed in accordance with the present description. The device is embodied in a system 100 that comprises an electromagnetic (EM) field generator 101, a microcurrent generator 104, and a photonic accumulator 106. A power supply 108 provides electrical power for the EM field generator 101, the microcurrent generator 104, and the photonic accumulator 106. The power supply 108 may also include an optional timer 108a to automatically time the therapeutic treatment of the subject. The timer 108a is a conventional component that may be implemented in a variety of different manners. For example, the timer 108a may comprise a push button (not shown) that automatically activates the system 100 for a predetermined time period when the push button is activated. Alternatively, the timer 108a may include a motor and a knob, which the user turns to the desired time of therapeutic treatment. Other alternatives may be used to implement the timer 108a, which need not be described in greater detail herein.

As will be described in greater detail below, the EM field generator 101 generates a broadband EM field with a power density ranging from low frequencies (i.e., a few hertz) to frequencies in the gigahertz range. In an exemplary embodiment, the power density ranges from less than 100 hertz to more than 1.0 gigahertz. The broadband EM field created by the EM field generator 101 substantially surrounds the subject thus exposing the subject to the wideband EM field.

Electromagnetic fields are increasingly being used to treat diseases in both human and animal subjects. Individual cells in a subject function in an electrical environment which influences the health of the cells. The electrical environment of the cells may be modified by placing the subject in the proximity of an electromagnetic (EM) field. It is believed that the presence of an EM field has a beneficial impact on diseased or damaged cells and, therefore, a need exists for a device to generate an appropriate EM field and a method for treating subjects with the EM field generated by the device.

Because the reaction of various types of cells is frequency dependent, the present invention advantageously provides a wide spectrum of harmonics up to approximately 2 GHz. Although not intended to be limited by the following theory, the physiological basis for the effectiveness of the present invention is believed to be as follows: at a cellular level, magnetic fields penetrating the body generate microcurrents that are incrementally rectified by the non-linear impedance of cell membranes in such a manner as to increase TMP, and consequently ATP production, in effect heightening the cell's bioenergy.

At a molecular level, the alternating electrical field (1) at some specific frequency within the broad spectrum of EM energy may excite specific molecular resonance such as to accelerate biochemical processes, and/or (2) the bipolar oscillations of the electric fields may excite mechanical vibrations of electrically charged molecules (anions/cations) in the tissues to produce acoustic energy that operates to increase blood flow and membrane permeability (electrophoresis). At an atomic level, the alternating magnetic fields may affect electron spin and/or linkage bonds in such a manner as to expedite biochemical processes.

At the same time, the subject is posited in contact with electrodes from the microcurrent generator 104, which generates a wideband microcurrent. Although not intended to be limited by the following theory, the physiological basis for the effectiveness of the microcurrent is believed to be as follows:

As the microcurrents at broadband frequencies pass through the subject, it activates energy meridians within the body. Energy meridians form the basis of acupuncture and acupressure treatment wherein the acupuncture/acupressure activates meridians at points of energy blockage to balance energy flow in the body and thereby activate self healing mechanisms. Similarly, the microcurrents generated by the microcurrent generator 104 are believed to activate meridians and thus activate the body's own self healing mechanisms.

Furthermore, it is known that the human body emits a form of EM energy that may be described as an auric field. This auric field may be visualized using known technologies, such as Kirlian photography and other modalities. Scientists have determined that the EM energy emitted from the body is the result of photons circulating among molecules and being passed from one atom to another. Scientists hypothesize that molecules, including deoxyribonucleic acid (DNA) may function as selective resonators for photon information and energy. For example, it is known that in the presence of structural subluxations of the cranium, spine, extremities, muscular spasms and ligamentous inflammation, there is an alteration and intensification of light emissions at the point of dysfunction. As noted above, Kirlian photography may be used to indicate the presence of such dysfunctions.

Despite the ability to measure such variations in photonic emission from the body, there is presently no suitable mechanism for utilizing this information to activate healing processes within the body. The photonic accumulator 106 uses coherent light to interact with the information contained in a portion of the photonic emissions from the body. Although not intended to be limited by the following theory, the physiological basis for the effectiveness of certain coherent light interaction with bio-photons is that new information is reflected back to the body to activate self-healing processes within the body.

Bio-photonic light was discovered by the Russian Alexander Gurvich in 1922. Fritz-Albert Popp described it as "bio-laser light emanating from the DNA of every living cell." Bio-photons, as he called them, are information transmitters within and outside the living organism. He says biophoton emission is a general phenomenon of living systems. It concerns low luminescence from a few up to some hundred photons per second, per square centimeter surface area, at least within the spectral region from 200 to 800 nm. The experimental results indicate that biophotons originate from a coherent (or/and squeezed) photon field within the living organism, its function being intra and intercellular regulation and communication.

In their book "The Living Energy Universe," Drs. Schwartz and Russek describe that human DNA may function as a transmitter and receiver for this class of photons called biophotons. The reprogramming of information contained in the bio-photonic field emitted from the body can communicate back information which assists in biologic retrieval and reprogramming of systems and tissues to aid in their return to correct functionality. The present invention is directed to a technique to activate the body's self-healing mechanisms through the use of monochromatic and/or coherent light and reflective surfaces to reprogram the information contained in the body's own bio-photonic field.

For example, reprogramming the intensified light emissions at the point of dysfunction, such as are known to occur in the locale of muscular spasms and ligamentous inflammation, communicates information to the body to correct the dysfunction and thus assists in the self-healing process.

Figure 2A:
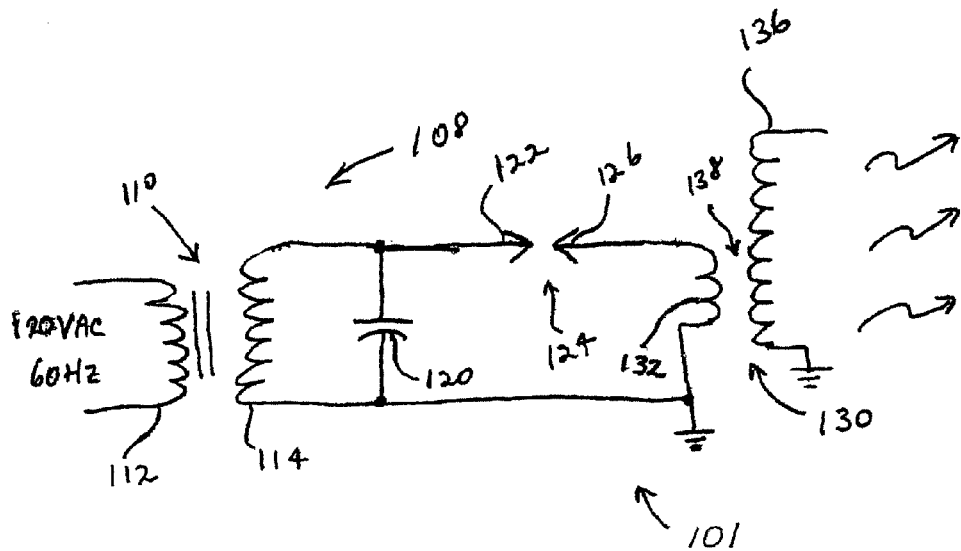
FIG. 2A is a circuit diagram of a portion of the circuit of FIG. 1.

One version of an EM field generator 101 is shown in the circuit diagram of FIG. 2A. While the functional block diagram of FIG. 1 illustrates a single power supply 108, the power supplies for the various portions of the system 100 are illustrated separately for the sake of clarity. Those skilled in the art will recognize that the various power supplies may be provided individually or as a portion of a single power supply. As illustrated in FIG. 2A, the power supply 108 includes a transformer 110 having a primary winding 112 coupled through a magnetic core to a secondary winding 114. In an exemplary embodiment, the transformer 110 is a step-up transformer having an input configured for operation with a 120-volt AC source and designed for connection to a conventional AC outlet.

The system 100 is described herein for connection with a conventional power source found in the United States and other countries. However, the present invention is not limited to use in those countries. Those skilled in the art will recognize that the power supply 108 may be readily adapted for operation in other countries, such as European countries where the standard voltage and frequency are somewhat different. However, these are minor design choices well within the scope of knowledge of one of ordinary skill in the art. Power switches, plugs, fuses and the like are typically included in the power supply 108, but are omitted here for the sake of brevity.

The secondary of the transformer 110 generates approximately 6,000 volts AC. The outputs of the secondary winding 114 are coupled to the plates of a capacitor 120. A first end of the capacitor 120 is coupled to a first terminal 122 of a spark gap 124. An air core resonant transformer 130 is coupled to the power supply 108 through a second terminal 126 of the spark gap 124. Specifically, the second terminal 126 is coupled to a first end of an inductor 132. A second end of the variable inductor 132 is connected to the circuit ground along with the second end of the capacitor 120 and one end of the secondary winding 114.

The inductor 132 is coupled to a Tesla coil 136 across an air gap 138. In practice, the air gap 138 is made as possible to minimize losses in the coupling. However, the air gap 138 must be large enough to prevent arcing between the inductor 132 and the Tesla coil 136. In addition, the inductor 132 may be tuned for optimal operation with the Tesla coil 136. A first end of the Tesla coil 136 is coupled to the circuit ground while the second end of the Tesla coil is open to thereby generate the broadband EM field.

Figure 2B:
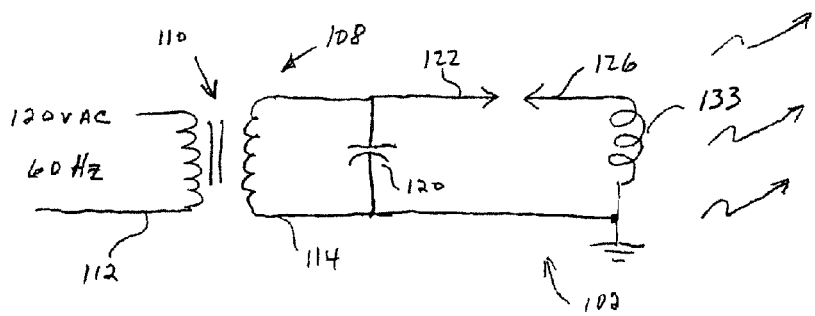
FIG. 2B is a circuit diagram of an alternative body of a portion of the circuit of FIG. 1.

In an alternative embodiment of the EM generator 102 as illustrated in FIG. 2B, the air core resonant transformer and Tesla coil are not used. All other components are identical to those in FIG. 2A. The outputs of the secondary winding 114 are coupled to the plates of the capacitor 120. A first end of the capacitor 120 is coupled to the first terminal 122 of the spark gap 124. The second terminal 126 is coupled to the first end of an inductor 133. The second end of the inductor 133 is connected to the circuit ground along with the second end of the capacitor 120 and one end of the secondary winding 114A. In this embodiment, the inductor 133 and spark gap 124 generate the broadband EM field.

Figure 3:
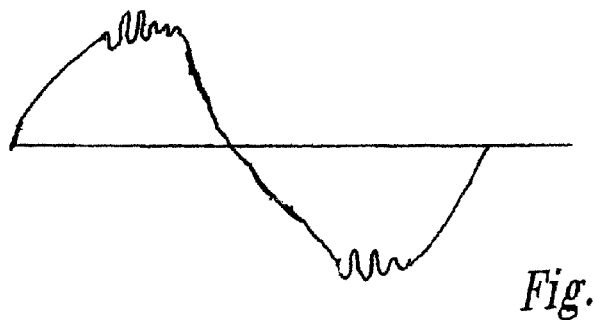
FIG. 3 is a timing waveform illustrating the operation of the circuit of FIG. 2A.

FIG. 3 illustrates a timing wareform of the EF field generator 101. The voltage on the capacitor 120 rises until it exceeds the threshold required to arc across the spark gap 124. The first and second electrodes 122 and 126 may be positioned with respect to each other to provide control over the arc voltage. When the voltage arcs across the spark gap 124, a broadband radiation is generated. Thus, the EM radiation is pulsed EM radiation at a pulse rate determined by the line frequency (e.g., 60 Hz). The EM radiation may be thought of as "natural" frequencies since they are dictated by the characteristics of the conductor (i.e., the air surrounding the spark gap 124). In an exemplary embodiment, electrical wire coupling the transformer 110 to the capacitor 120 and the spark gap 124 are spark plug wires, which have an inherent resistance. Thus, the capacitor 120 is charged at a rate determined by the resistance of the connecting wires and the value of the capacitance. In an exemplary embodiment, the capacitor 120 has a value of 0.01 microfarads and the wire used for interconnections has a resistance of approximately 100 ohms. Those skilled in the art will recognize that changes may be made in the resistance or capacitance values without adversely affecting operation of the system 100. The circuit of FIG. 2B generates a substantially identical wave form and operates in the manner described above with respect to the circuit of FIG. 2A with the only exception being that the inductor 133 is configured to generate the EM field without the need for the Tesla coil 136 or the air gap 138 of FIG. 2A.

Figure 4:
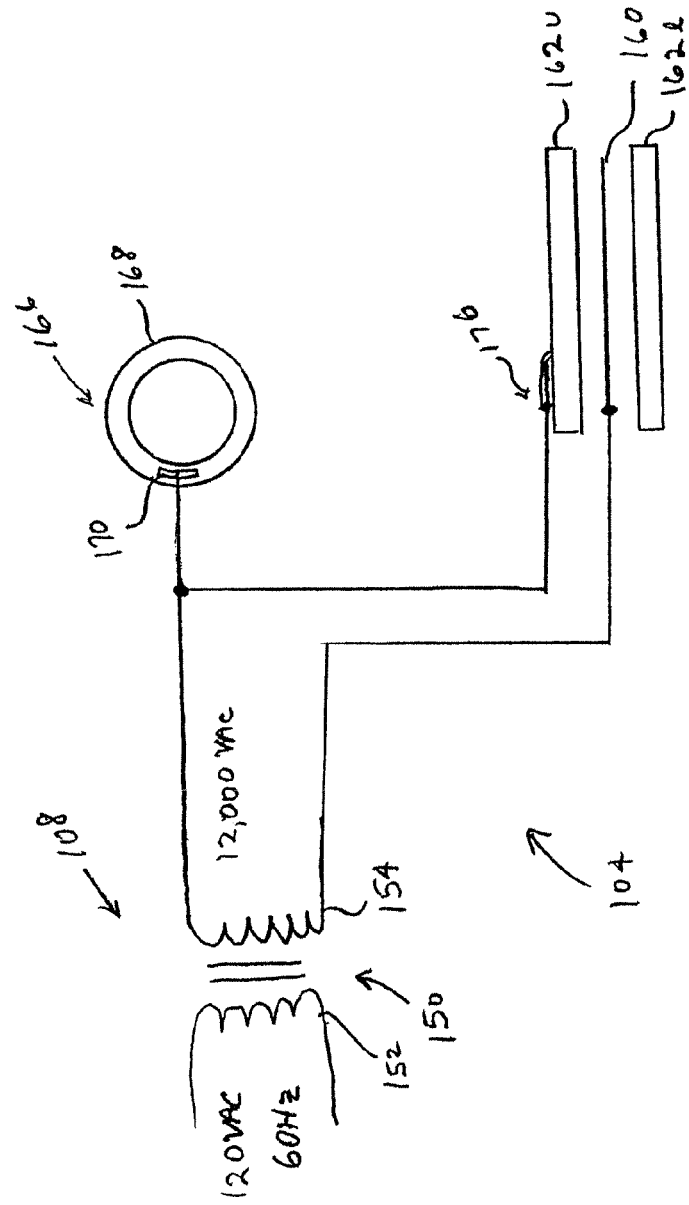
FIG. 4 is a circuit diagram of a portion of the circuit of FIG. 1.

Details of the microcurrent generator 104 are shown in the circuit diagram of FIG. 4. As previously discussed, the power supply 108 of FIG. 1 may be implemented as a series of independent power supplies or incorporated into a single integrated power supply. Returning to FIG. 4, the power supply 108 comprises a transformer 150 having a primary winding 152 coupled through a magnetic core to a secondary winding 154. In an exemplary embodiment, the transformer 150 is a step-up transformer having an input configured for connection to a 120 volt AC source. The secondary of the transformer 150 generates approximately 12,000 volts AC. As discussed above with respect to the EM generator 101, spark plug wire is used for the electrical conductors in the microcurrent generator 104.

One side of the secondary winding 154 is coupled to an electrode 160. In an exemplary embodiment, the electrode 160 is a foil conductor, such as a gold foil conductor. The electrode 160 is sandwiched between an upper glass plate 162u and a lower glass plate 162l. In an exemplary embodiment, the upper and lower glass plates 162u and 162l are 3/16 inch-thick tempered glass plates.

The other side of the secondary winding 154 is coupled to a hand-held electrode 166 and to a spark gap generator 176. The hand-held electrode may be implemented by a circular fluorescent tube 168 in which electrodes 170 are coupled together and connected to the secondary winding 154 of the transformer 150. A conventional fluorescent tube 168 contains Mercury in a vapor state. However, the fluorescent tube 168 may contain other gases, such as Xenon in addition to or as a substitute for Mercury. Alternatively, the fluorescent tube 168 may contain other conventional gases and phosphors. Knowledge of fluorescent tubes and their operations within the knowledge of ordinary skill in the art need not be described in greater detail herein. Operational details of the system 100 using the hand-held electrode 166 are provided below.

Coupled in parallel with the hand-held electrode 166 is a spark gap 176. The spark gap electrode 176 is maintained in physical contact with the upper glass plate 162u. Those skilled in the art will recognize that the spark gap electrode 176 and the electrode 160 are positioned on opposite sides of the upper glass plate 162u thus forming a capacitor in which the upper glass plate is a dielectric material between the two conductors (i.e., the electrode 160 and the spark gap electrode 176).

Figure 5:
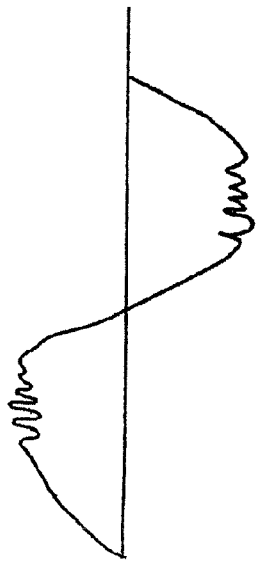
FIG. 5 is a timing waveform illustrating the operation of the circuit of FIG. 4.

In operation, the voltage produced by the secondary winding 154 is applied to the electrode 160 and the spark gap electrode 176. As the voltage between the electrode 160 and the spark gap electrode 176 increases, arcing occurs from the spark gap electrode. FIG. 5 illustrates a timing waveform of the microcurrent generator 104. The voltage on the spark gap electrode 176 increases until arcing occurs generating broadband microcurrents. As discussed above with respect to the EM field generator 101, the microcurrent generator 104 generates microcurrents at natural frequencies, which are dictated by the characteristics of the conductor (i.e., the air surrounding the spark gap electrode 176).

In one embodiment, the transformers 110 and 150 are arranged so that the electromagnetic field generated by the EM field generator 101 and the microcurrent generated by the microcurrent generator 104 are in phase. This can be done simply by arranging the leads of the secondary windings so as to provide the proper phasing in the power supply 108 for the transformers 110 and 150. Alternatively, the electromagnetic field generated by the EM field generator 102 and the microcurrent generated by the microcurrent generator 104 may be arranged so as to operate out of phase with respect to each other. In yet another alternative embodiment, a switch (not shown) may be used to adjust the phasing of the EM field generator 102 and microcurrent generator 104 so as to be in phase or out of phase at the discretion of the operator.

Details of construction of the spark gap conductor 176 are illustrated in FIGS. 6 and 7. FIG. 6 is a top plan view illustrating a fragmentary portion of the upper glass plate 162u and the spark gap electrode 176. In an exemplary embodiment, the spark gap electrode 176 is formed from a copper plate and is substantially rectangular in shape with one or more projections 180 extending from one of the long sides of the rectangularly shaped spark gap electrode 176. As best seen in FIG. 7, which is a side view of the spark gap electrode 176, the projections 180 are curved and extend downward toward the upper glass plate 162u. In this manner, the current density is maximized at the projections 180 and is the point at which arcing occurs. The spark gap electrode 176 also includes an aperture 182 to permit the connection of electrical wiring. The aperture 182 may also serve to retain the spark gap electrode 176 in position with respect to the upper glass plate 162u. Alternatively, the spark gap electrode 176 may be fixed in position using a clamp (not shown), or other conventional mechanical retention device. Care must be taken not to short out the spark gap electrode 176.

Figure 8:
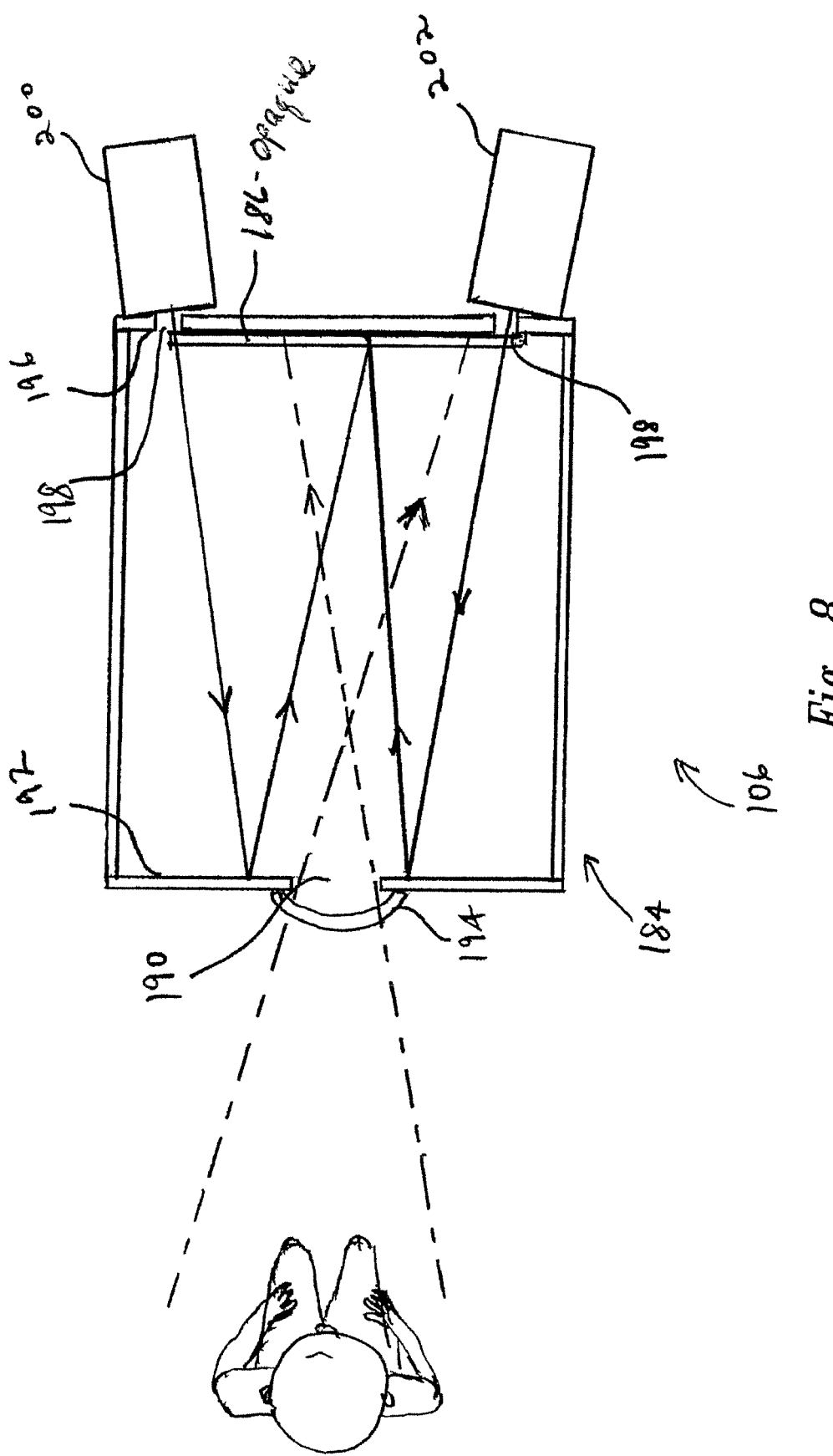
FIG. 8 is a top plan view of a photonic accumulator.

FIG. 8 is a top plan view of the photonic accumulator 106, which is contained within a housing 184. Although the precise shape of the photonic accumulator housing 184 is not critical to satisfactory operation of the system 100, in an exemplary embodiment, the photonic accumulator 106 is substantially rectangular in shape and contains an aperture 190 in a front wall 192 facing the subject. A lens 194 may be positioned in association with the aperture 190 to focus photonic emissions from the subject onto a rear wall 196 of the photonic accumulator 106. In an exemplary embodiment, the front wall 192 and rear wall 196 are covered with a reflective surface, such as a mirror, to reflect photons. Alternatively, all interior surfaces of the photonic accumulator 106 may be coated with reflective surfaces.

The rear wall 196 of the photonic accumulator 106 contains a pair of apertures 198 to permit the introduction of light into the photonic accumulator 106. A light source 200 is positioned adjacent one of the rear apertures 198 and produces visible light. In an exemplary embodiment, the light source 200 is a coherent light source producing light having a wavelength of approximately 650 nm. The light source 200 is positioned so as to direct the light off the reflective front wall 192. The reflective surfaces on the front and rear walls 192 and 196 cause the light from the light source 200 to be reflected multiple times within the photonic accumulator 106 thereby enhancing activation of biophotons emitted from the subject.

In addition, a light source 202 is positioned adjacent the second rear aperture 198 to deliver additional light into the photonic accumulator 106. In an exemplary embodiment, the light source 202 is a coherent infrared light source having a wavelength of approximately 805 nm. The light source 202 is also positioned to direct light onto the reflective front surface 192. Thus, the light sources 200 and 202 direct light into the photonic accumulator 106 for interaction with biophotons emitted from the subject.

The light sources 200 and 202 are readily powered by a low voltage DC power supply (not shown), which forms a portion of the power supply 108, illustrated in FIG. 1. In an alternative embodiment, only one of the light sources 200-202 is provided and thus only one of the apertures 198 in required in the rear wall 196. In yet another alternative embodiment, the light sources 200 and 202 are placed within the interior portion of the photonic accumulator 106 thus eliminating the need for the apertures 196 and 198.

Although not limited to this theory of operation, it is believed that the activated biophotons communicate back to the biophotons in the subject via quantum entanglement to enable activation of the body's self-healing mechanisms.

Figure 9:
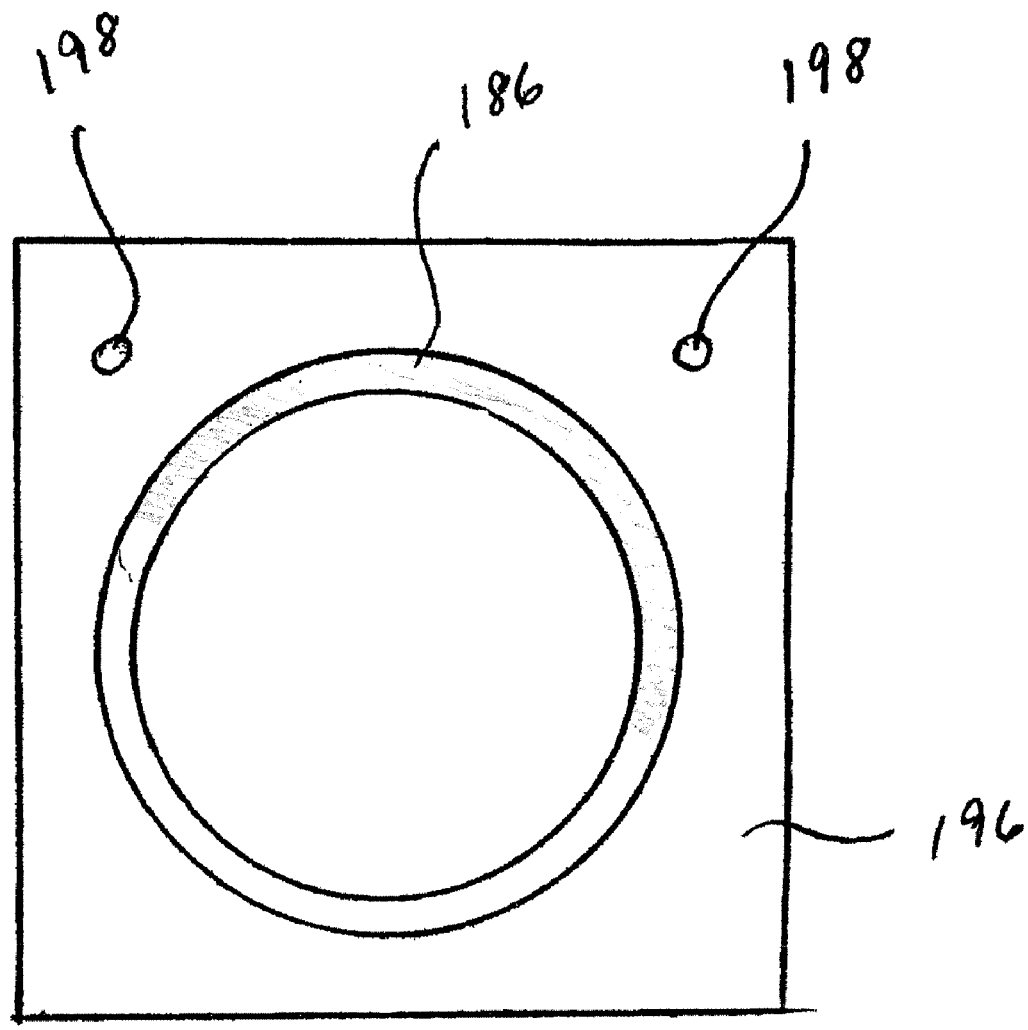
FIG. 9 is a plan view of the rear wall of the photonic accumulator of FIG. 8.

As best seen in FIG. 9, the rear wall 196 of the housing 184 includes an opaque member 186, which serves to define a limited area at which the photonic emissions from the subject will be directed. The opaque member 186 may be satisfactorily implemented using a variety of techniques. In one embodiment, the opaque member 186 may be a black circular O-ring, which may be manufactured from rubber or other suitable pliable material. The specific type of material used to implement the opaque member is not critical to satisfactory operation of the invention. Furthermore, the opaque member 186 may be designed to have a shape other than a circular shape. Light from the light sources 200 and 202 are reflected off the reflective surface of the front wall 192 and into an area of the rear wall 196 within the opaque member 186.

Figure 10:
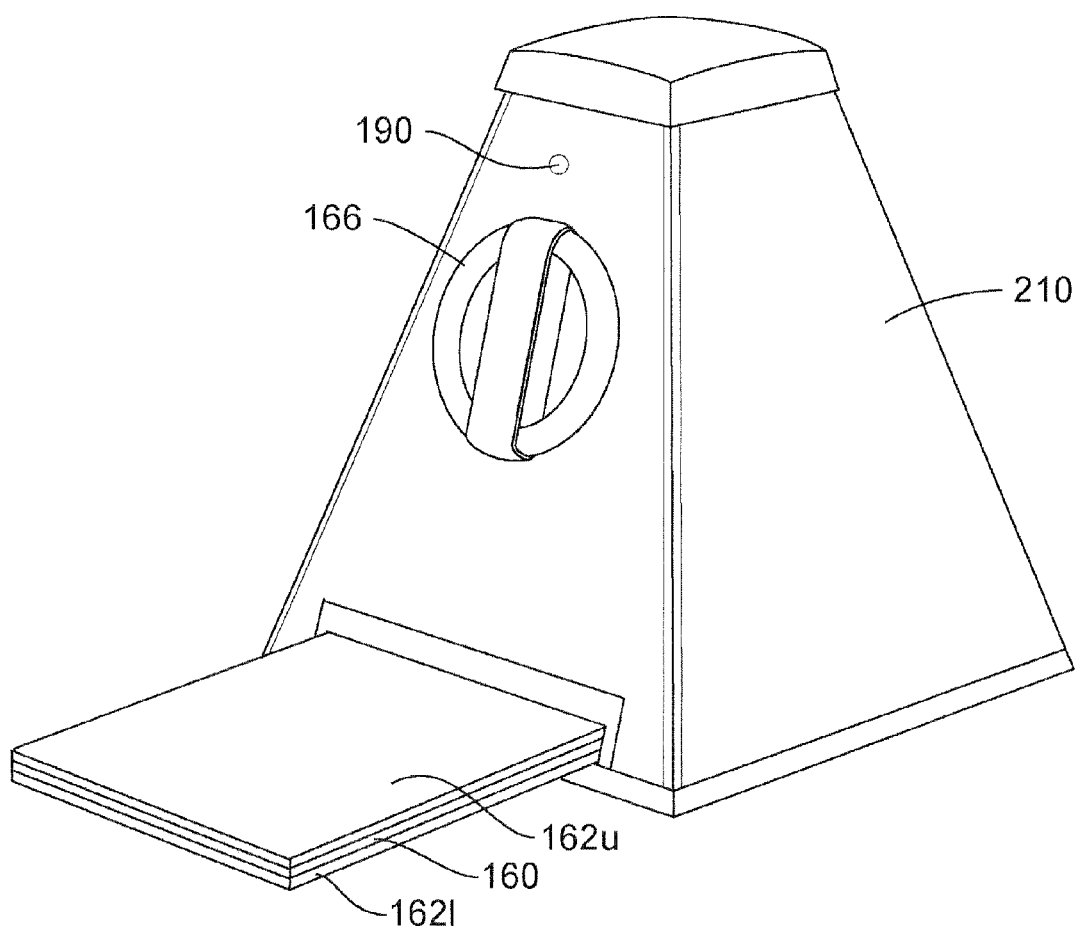
FIG. 10 is a perspective view of the device of FIG. 1.

FIG. 10 is a perspective view of a housing 210 containing the system 100. The electronics, including the EM field generator 101, microcurrent generator 104, photonic accumulator 106 and power supply 108 are all contained within the housing 210. In the embodiment illustrated in FIG. 10, the microcurrent electrodes are exposed for operation with the subject. The electrode 160 sandwiched between the glass plates 162u and 162l are roller mounted to extend from within the housing during operation. For storage purposes, the electrode 160 and glass plates 162u and 162l may be stored within the housing 210. The hand-held electrode 166 may be conveniently mounted on an external portion of the housing 210 using any convenient mechanism, such as a hook, Velcro, or other fastener. These fasteners are conventional in operation and need not be described or illustrated herein.

Figure 11:
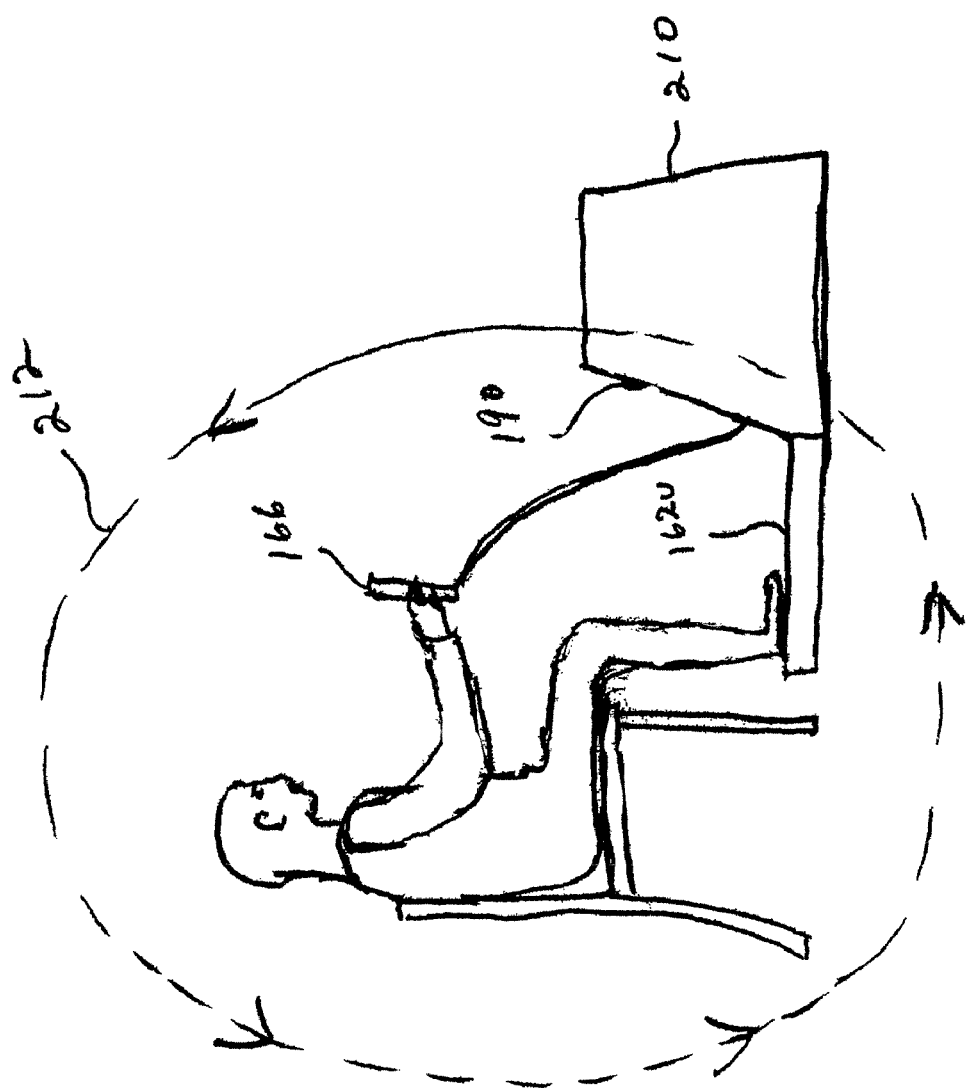
FIG. 11 is a side view of the housing of FIG. 9 illustrating the placement of the subject for operation with the system.

In operation, the electrode 160 and glass plates 162u and 162l are extracted from the housing 210 and positioned adjacent the subject. The hand-held electrode 166 may be removed from its mounting position on the external portion of the housing 210 and held by the subject. The operation of the system 100 may be best understood with respect to FIG. 11, which is a side view of the housing 210. The subject is positioned adjacent the housing 210 to permit placement of the subject's bare feet on the upper glass plate 162u. During operation of the system 100, the subject grasps the hand-held electrode 166 thereby inducing microcurrents to flow between the electrode 160 and the hand-held electrode 166 via the subject. As previously discussed, it is believed that the broadband microcurrents activate energy meridians within the subject to thereby promote self-healing. In addition, the EM field generator 101 (see FIG. 1) within the housing 210 generates an EM field, roughly illustrated by a reference numeral 212 in FIG. 11. Those skilled in the art will recognize that a multitude of electromagnetic field lines generated by the EM field generator 101 will envelope the subject. However, for the sake of simplicity, the multiple electromagnetic lines are illustrated as the EM field 212.

During the period of time during which the subject in exposed to the electromagnetic field 212 and receives the microcurrent from the microcurrent generator 104, biophotons emitted from the subject are delivered through the aperture 190 in the housing 212 into the photonic accumulator 106, as described above. The biophotons collected by the photonic accumulator 106 are exposed to the light sources 200 and 210 (see FIG. 8) as previously discussed.

Figure 12:
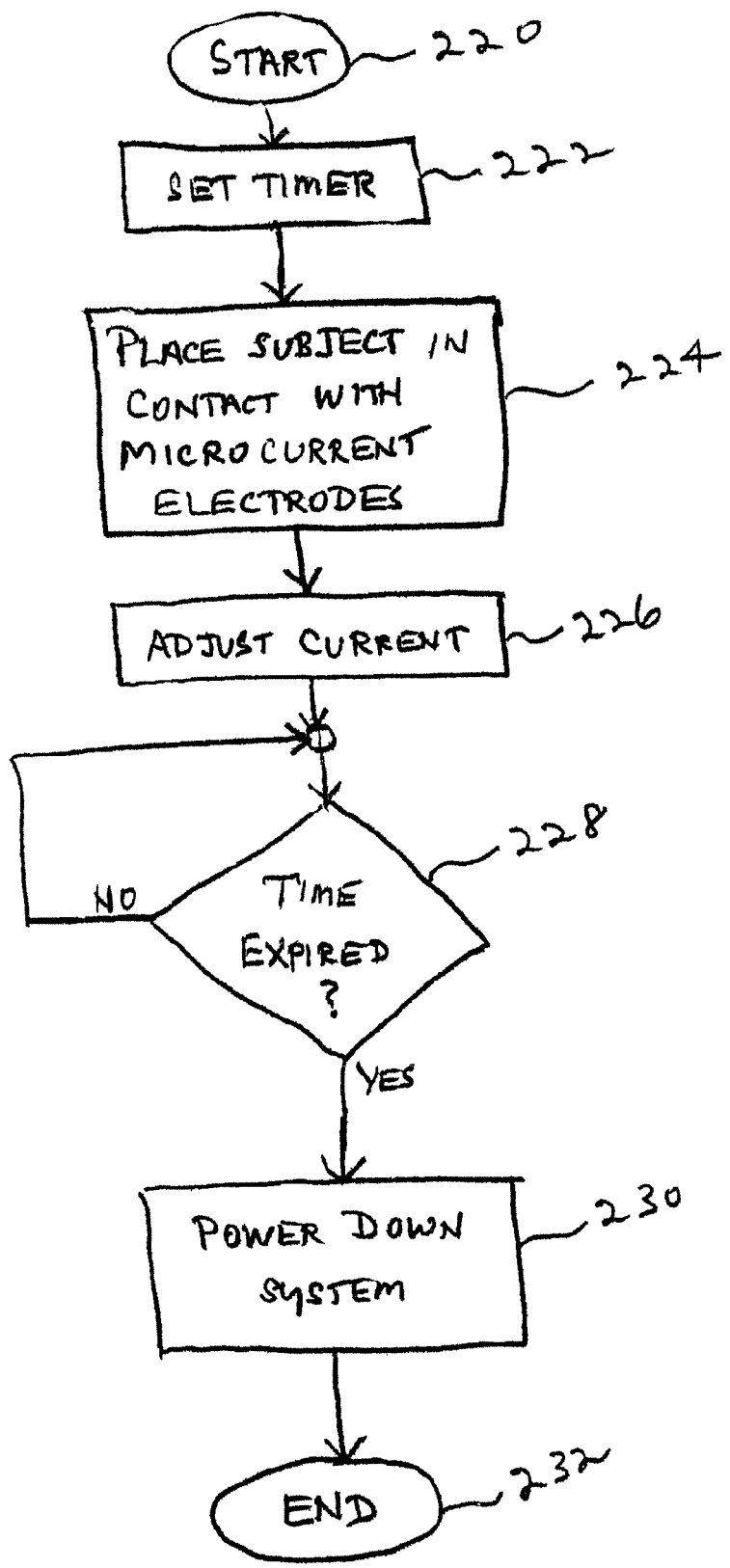
FIG. 12 is a flow chart illustrating the operation of an exemplary embodiment of a device constructed in accordance with the present description.
Figure 13:
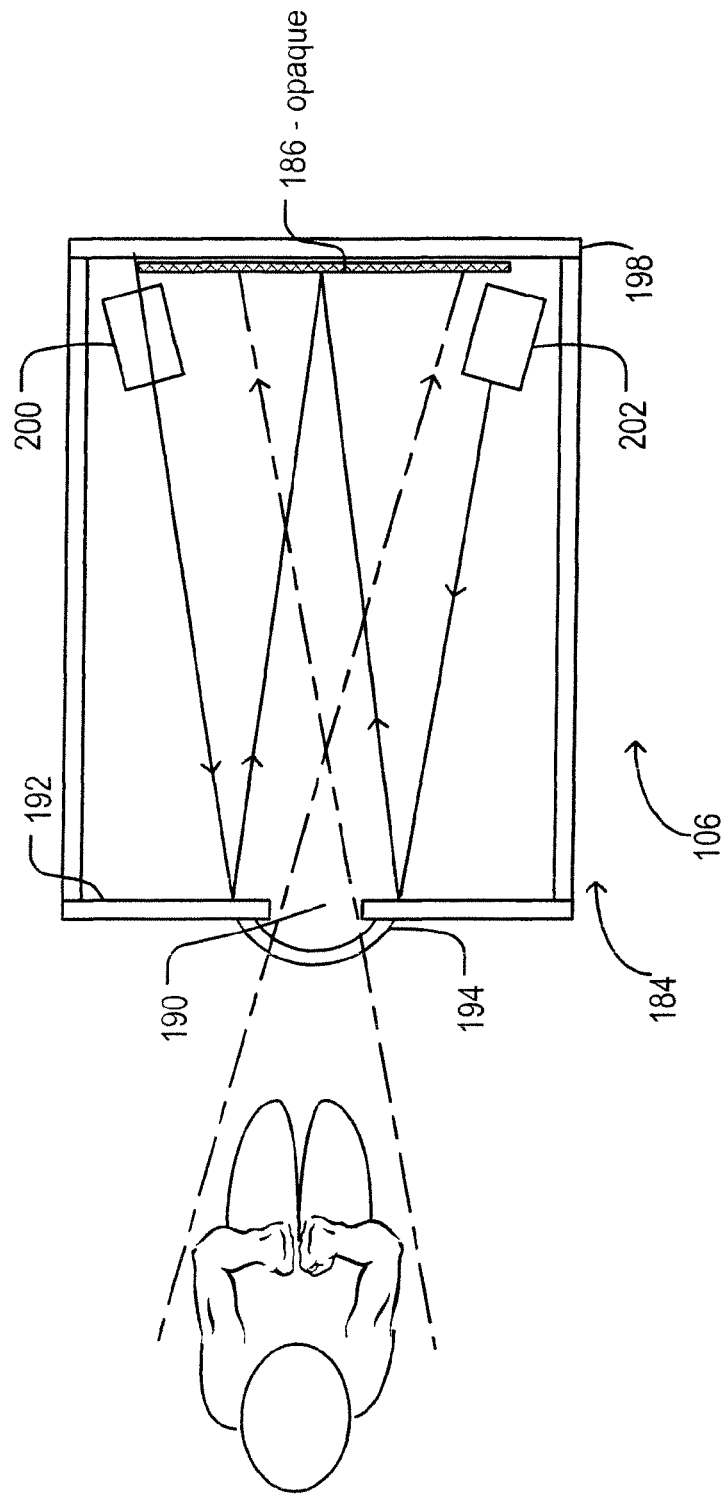
FIG. 13 is a top plan view of an alternative embodiment photonic accumulator.

The subject receives treatment by the system 100 for a therapeutic period of time. The operation of the system 100 is illustrated in the flowchart of FIG. 12 where at a start 220, the subject is placed in position proximate the housing 210 so as to be within the electromagnetic field 212 when the system is activated. At step 222, the subject or an operator sets the timer 108a (see FIG. 1) for a therapeutic period of time. In one example, the subject may receive preliminary dosages of approximately 5-10 minutes. The period of time may be lengthened or shortened as appropriate. In step 224, the subject is placed in contact with the microcurrent electrodes (e.g., the electrode 160 via the upper glass plate 162u and the hand-held electrode 166).

In step 226, the microcurrent is adjusted. The microcurrent generator 104 is limited in current to approximately 2500 microamps. In practice, the user can control the level of microcurrent by adjusting the tightness with which the subject grasps the hand-held electrode 166. The user may also adjust the level of microcurrent by regulating the amount of contact between the subject's feet and the upper glass plate 162u. For example, placing both feet firmly on the upper glass plate 162u will maximize the microcurrent flowing through the subject. Removing one foot or rolling the subject's feet so that only a portion of the feet make contact with the upper glass plate 162u will effectively reduce the level of microcurrent. Thus, the microcurrent generator 104 can be readily adjusted to the comfort level of the subject.

In decision 228, the system determines whether the time has expired. If the time has not expired, the result of decision 228 is NO and the system returns to the beginning of decision 228 until the therapeutic period of time has expired. During this time, the subject is exposed to both the electromagnetic field 212, and receives the microcurrent from the microcurrent generator 104. In addition, biophotons emitted from the subject are accumulated by the photonic accumulator 106 and enhanced or activated by the light sources 200 and 202.

When the therapeutic period of time has expired, the result of decision 228 is YES. In that event, in step 230, the power supply 108 is deactivated so as to terminate the electromagnetic field, the microcurrent, and the light sources 200 and 202 in the photonic accumulator 106. The process ends at 232.

Thus, the system 100 provides a technique by which the subject may be exposed in safe dosages to broadband electromagnetic fields, microcurrents, and receives activated biophotons. The process may be repeated as needed.

All of the above U.S. patents, U.S. patent application publications, and U.S. patent applications referred to in this specification are incorporated herein by reference in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for physiologic treatment of a living subject comprising:
    generating an electromagnetic field around the subject for a therapeutic period of time;
    generating a microcurrent and applying the microcurrent to the subject for the therapeutic period of time;
    accumulating photons emitted by the subject for the therapeutic period of time, wherein the accumulating photons comprises providing a substantially planar target surface proximate the subject, the target surface including an opaque member disposed thereon having a simple closed shape so as to define a limited target area on the target surface within the opaque member; and directing the photons emitted by the subject through an aperture toward the target area of the target surface; and
    generating a light to interact with the emitted photons, the light generating comprising directing the light toward the target area to interact with the emitted photons; and shielding the light so that it cannot impinge directly on the subject, wherein the light comprises a beam of collimated, coherent light.

2. The method of claim 1, wherein the opaque member is black and has an approximately circular shape.

3. The method of claim 1, wherein the generating the electromagnetic field comprises generating a spark.

4. The method of claim 1, wherein the generating the microcurrent comprises generating a spark.

5. The method of claim 1, further comprising:
    contacting the subject with a first microcurrent electrode and a second microcurrent electrode; and
    positioning the first microcurrent electrode and the second microcurrent electrode so that at least a portion of the generated microcurrent passes from the first electrode to the second electrode via the subject for the therapeutic period of time.

6. The method of claim 1, generating the electromagnetic field and generating the microcurrent comprising:
    generating the electromagnetic field and generating the microcurrent in-phase with respect to each other.

7. The method of claim 1, generating the electromagnetic field and generating the microcurrent comprising:
    generating the electromagnetic field and generating the microcurrent out-of-phase with respect to each other.

8. A method for physiologic treatment of subluxations or injuries in a human or animal subject comprising:
    providing a substantially planar target surface;
    disposing an opaque member having a simple closed shape onto the target surface so as to define a limited target area on the target surface within the opaque member;
    focusing biophotons naturally emitted by the subject toward the target area of the target surface;
    directing a beam of collimated, coherent light toward the target area to interact with the naturally emitted biophotons; and
    shielding the beam of collimated, coherent light so that it cannot impinge directly on the subject.

9. The method of claim 8 further comprising:
generating an electromagnetic field around the subject;
generating a microcurrent and applying the microcurrent to the subject.

10. The method of claim 8, shielding the beam of collimated, coherent light comprising:
enclosing the target surface within a substantially closed housing, the housing including an aperture to permit entry of the naturally emitted biophotons such that they impinge the target area.

11. The method of claim 8 wherein the opaque member is black and has an approximately circular shape.

12. The method of claim 8 wherein beam of collimated, coherent light is visible light.

13. The method of claim 12 further comprising:
directing a second beam of collimated, coherent light toward the target area to interact with the naturally emitted biophotons; and
shielding the second beam of collimated, coherent light so that it cannot impinge directly on the subject.

14. The method of claim 13 wherein the second beam of collimated, coherent light is infrared.

* * * * *